US008101803B2

(12) United States Patent
McConnell et al.

(10) Patent No.: US 8,101,803 B2
(45) Date of Patent: Jan. 24, 2012

(54) PROCESS FOR THE ADDITION OF THIOLATES TO α,β-UNSATURATED CARBONYL OR SULFONYL COMPOUNDS

(75) Inventors: James R. McConnell, Midland, MI (US); Douglas C. Bland, Midland, MI (US)

(73) Assignee: Dow AgroSciences LLC, Indianapolis, IN (US)

( * ) Notice: Subject to any disclaimer, the term of this patent is extended or adjusted under 35 U.S.C. 154(b) by 35 days.

(21) Appl. No.: 12/537,274

(22) Filed: Aug. 7, 2009

(65) Prior Publication Data

US 2010/0048939 A1    Feb. 25, 2010

Related U.S. Application Data

(60) Provisional application No. 61/090,045, filed on Aug. 19, 2008.

(51) Int. Cl.
C07C 319/02    (2006.01)
(52) U.S. Cl. .......................................................... 568/41
(58) Field of Classification Search ...................... 568/41
See application file for complete search history.

(56) References Cited

U.S. PATENT DOCUMENTS

| 4,944,853 A | 7/1990 | Sandler |
| 5,705,675 A | 1/1998 | Blackburn et al. |

FOREIGN PATENT DOCUMENTS

| DE | 855704 | 9/1952 |
| DE | 2338680 | 2/1974 |
| DE | 3627410 | 2/1987 |
| FR | 976673 | 3/1951 |
| WO | 96/040631 | 12/1996 |
| WO | US2009/053061 | 10/2009 |

OTHER PUBLICATIONS

Delp et al, Inorganic Chemistry, 2007, 46(7), 2365-2367.*
Tye et al, Helvetica Chimica Acta, 2002, 85(10), 3272-3282.*
Hall, R. H. and Howe, B. K.; "Reactions of Crotonaldehyde with Ethanethiol." J. Chem Society, 1949, pp. 2723-2724.
Brown, R.; Jones, W.E.; and Pinder, A.R.; "The Addition of Toluene-w-thiol to Unsaturated Compounds." J. Chemical Society, 1951, pp. 3315-3318.
Bateman, L; Cunneen, J. I.; and Ford, J; "Oxidation of Organic Sulphides. Part VII. The Mechanism of Autoxidation of But-2-enyl Methyl Sulphide, Methyl 1-Methyl-but-2-enyl Sulphide, and n-Butyl Methyl Sulphide."J. Chem Society, 1956, pp. 3056-3064.
Reisner, David B.; "Sulfur-Containing Amino Acids." J. Amer. Chem. Soc. vol. 78, 1956, pp. 2132-2135.
Boustany, K.S.; "Addition of Methanethiol to Some . . . Unsaturated Aldehydes and Study of the Reduction and Acetalisation of the Addition Products." J. Chem. U.A.R., 9. No. 3, 1966, pp. 317-322.
Badings, H. T.; Maarse, H.; Kleipool, R.J.C.; Tas, A.C.; Neeter, R.; Ten Noever De Brauw, M.C.; "Formation of Odorous Compounds from Hydrogen Sulphide and Methanthiol, and Unsaturated Carbonyls." Proc. int. Symp. Aroma Research, Zeist, 1975, pp. 63-73, Pudoc, Wageningen.
Jacob, L.; Julia, M.; Pfeiffer, B. and Rolando, C.; "On the Influence of Phosphoric Ester Groups in Geranyldiphosphate Biosynthesis." Bull Soc Chim Fr, 127, 1990, pp. 719-733.
Ranu, Bridaban C.; Dey, Suvendu S.; and Hajra, Alakananda; "Catalysis by an Ionic Liquid: Efficient Conjugate Addition of Thiols to Electron Deficient Alkenes Catalyzed by Molten Tetrabutylammonium Bromide Under Solvent-Free Conditions." Tetrahedron 59, 2003, pp. 2417-2421.
Naidu, B. Narasimhulu; Sorenson, Margaret E.; Connolly, Timothy P.; and Ueda, Yasutsugu; "Michael Addition of Amines and Thiols to Dehydroalanine Amides: A Remarkable Rate Acceleration in Water." J. Org. Chem. 2003, 68. pp. 10098-10102.
Ranu, Brindabum C. and Dey, Suvendu S.; "Catalysis by Ionic Liquid: A Simple, Green and Efficient Procedure for the Michael Addition of Thiols and Thiophosphate to Conjugated Alkenes in Ionic Liquid, [pmlm]Br." Tetrahedron 60, 2004, pp. 4183-4188.
Ranu, Brindaban C. and Mandal, Tanmay; "Indium(I) Iodide-Promoted Cleavage of Dialkyl Disulfides and Subsequent Michael Addition of Thiolate Anions to Conjugated Carbonyl Compounds." SYNLETT 2004, No. 7, pp. 1239-1242.
Movassagh, Barahman and Zakinezhad, Yousef; "Formation of Zinc Thiolates by Reductive Cleavage of Disulfides with the Zn/AICI3 System in Aqueous Media, and their Use for Michael Addition." Verlag der Zeitschrift fur Naturforschung, Tubingen, 2006, pp. 47-49.
Willis, Michael C.; Randell-Sly, Helen E.; Woodward, Robert L.; McNally, Steven J.; and Currie, Gordon S.; "Rhodium-Catalyzed Intermolecular Chelation Controlled Alkene and Alkyne Hydroacylation . . . " J. Org. Chem., 2006, 71, pp. 5291-5297.
Ranu, Brindaban C. and Mandal, Tanmay; "Indium(I) Iodide Promoted Cleavage of Dialkyl Disulfides—Application of the Michael Addition of Thiolate Anions to Conjugated Carbonyl Compounds and Regioselective Ring Opening of Epoxides." Can. J. Chem. 84, 2006, pp. 762-770.
Lenardao, Eder J.; Ferreira, Patricia C.; Jacob, Raquel G.; Perin, Gelson and Leite, Fabio P.L.; "Solvent-Free Conjugated Addition of Thiols to Citral Using KF/Alumina: Preparation of 3-thioorganylcitronellals, Potential Antimicrobial Agents." Tetrahedron Letters 48, 2007, pp. 6763-6766. Ranu, Brindaban C. and Mandal, Tanmay; "Efficient Synthesis of B-Alkyl/Arylsuflanyl Carbonyl Compounds by In-TMSCI-Promoted Cleavage of Dialkyl/Diaryl Disulfides and Subsequent Michael Addition." Synthetic Communications, 37:9, 2007, pp. 1517-1523.
Schobert, Alfons and Lange, Gisela; On the Addition of Mercaptocarboxylic Acids to Unsaturated Acids[1], 1956.

* cited by examiner

Primary Examiner — Shailendra Kumar
(74) Attorney, Agent, or Firm — Carl D. Corvin; Craig E. Mixan

(57) ABSTRACT

Alkylthio substituted aldehydes, ketones, esters and sulfones are prepared by reacting α,β-unsaturated carbonyl and sulfonyl compounds with a sodium or potassium thiolate in the presence of a alkane carboxylic acid and water.

20 Claims, No Drawings

PROCESS FOR THE ADDITION OF THIOLATES TO α,β-UNSATURATED CARBONYL OR SULFONYL COMPOUNDS

This application claims the benefit of U.S. Provisional Application Ser. No. 61/090,045 filed on Aug. 19, 2008. The present invention concerns an improved process for the addition of sodium or potassium thiolates to α,β-unsaturated carbonyl or sulfonyl compounds.

BACKGROUND OF THE INVENTION

2-Trifluoromethyl-5-(1-alkylthio)alkylpyridines are useful intermediates for the preparation of certain new insecticides; see, for example, U.S. Patent Publications 2005/0228027 and 2007/0203191. Alkylthioenamines are useful intermediates for preparing 2-trifluoromethyl-5-(1-alkylthio)alkyl-pyridines; see, for example, U.S. Patent Publication 2008/0033180 A1. Alkylthioenamines can, in turn, be prepared by reacting an alkylthio substituted aldehyde with an anhydrous disubstituted amine. The alkylthio substituted aldehyde starting materials are difficult to obtain in high purity and are often contaminated with thioacetal and aldol condensation impurities. It would be desirable to have a process for preparing alkylthio substituted aldehydes in good yield and high purity.

SUMMARY OF THE INVENTION

The present invention concerns an improved process for the preparation of alkylthio substituted aldehydes, ketones, esters and sulfones of formula I

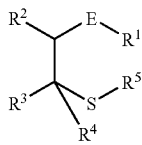

wherein

E represents CO or $SO_2$;

$R^1$ represents H, $C_1$-$C_8$ alkyl, $C_1$-$C_8$ alkoxy or aryl when E is CO and represents $C_1$-$C_8$ alkyl or aryl when E is $SO_2$; and $R^2$, $R^3$, $R^4$ and $R^5$ independently represent H, $C_1$-$C_8$ alkyl or aryl which comprises reacting an α,β-unsaturated carbonyl or sulfonyl compound of the formula II

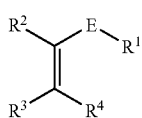

wherein

E, $R^1$, $R^2$, $R^3$ and $R^4$ are as previously defined with a sodium or potassium thiolate of formula III

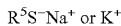

wherein $R^5$ is as previously defined in the presence of a $C_1$-$C_4$ alkane carboxylic acid and water. Preferably, E is CO, $R^1$ is H, $R^2$ is H, $CH_3$ or $CH_2CH_3$; $R^3$ is $CH_3$ or $CH_2CH_3$; $R^4$ is H; and $R^5$ is $CH_3$. The process may be conducted with or without a co-solvent.

DETAILED DESCRIPTION OF THE INVENTION

Unless specifically limited otherwise, the term "alkyl" (including derivative terms such as "alkane" and "alkoxy"), as used herein, include straight chain, branched chain, and cyclic groups. Thus, typical $C_1$-$C_4$ alkyl groups are methyl, ethyl, 1-methylethyl, propyl, 1,1-dimethylethyl, 1-methylpropyl, 2-methylpropyl, cyclopropyl and cyclobutyl. $C_5$-$C_8$ Alkyl groups additionally include, but are not limited to, pentyl, hexyl, heptyl, octyl, cyclopentyl, cyclohexyl, 1-methylhexyl, 2-ethylhexyl and 1-methylheptyl.

The term "aryl" refers to a phenyl, indanyl or naphthyl group, with phenyl being preferred. The aryl substituent may be unsubstituted or substituted with one or more substituents selected from halogen, hydroxy, nitro, cyano, aryloxy, $C_1$-$C_6$ alkyl, $C_1$-$C_6$ alkoxy, halogenated $C_1$-$C_6$ alkyl or halogenated $C_1$-$C_6$ alkoxy provided that the substituents are sterically compatible and the rules of chemical bonding and strain energy are satisfied.

$R^1$, $R^2$, $R^3$, $R^4$ and $R^5$ can be independently selected from the above alkyl and aryl substituents, again provided that the substituents are sterically compatible and the rules of chemical bonding and strain energy are satisfied.

In the present invention, alkylthio substituted aldehydes, ketones esters and sulfones are prepared by reacting α,β-unsaturated carbonyl or sulfonyl compounds with a sodium or potassium thiolate in the presence of an alkane carboxylic acid and water.

Approximately equimolar quantities of α,β-unsaturated carbonyl or sulfonyl compound and sodium or potassium thiolate are generally used in the process, although excesses of one or the other may be employed. In practice, a 1-50 percent, more preferably a 2-30 percent and most preferably a 3-20 percent stoichiometric excess of sodium or potassium thiolate is preferred. The alkane carboxylic acid is present in an amount equal to about 1 to 10 equivalents with respect to the limiting reagent, which may be either the α,β-unsaturated carbonyl or sulfonyl compound or the sodium or potassium thiolate. Typically, a 1.0-1.7 fold and more preferably a 1.1-1.6 fold excess of alkane carboxylic acid is preferred.

The reaction is conducted either in water alone or in the presence of an organic co-solvent. Preferred co-solvents are hydrocarbon solvents, most preferably aromatic hydrocarbons such as toluene. More polar solvents, such as acetonitrile, can also be employed.

The reaction is conducted at a temperature from about 0° C. to about 70° C. Temperatures from about 5° C. to about 60° C. are usually preferred.

The reaction is preferably conducted under a substantially oxygen-free atmosphere. More preferably the reaction is conducted under nitrogen.

In a typical reaction, the α,β-unsaturated carbonyl or sulfonyl compound and the alkane carboxylic acid and any optional co-solvent are mixed together and chilled to about 0 to about 5° C. An aqueous solution of sodium or potassium thiolate is added and the reaction is allowed to warm to room temperature and is stirred until the reaction is complete. The crude reaction mixture containing the alkylthio substituted carbonyl or sulfonyl compound can be isolated and purified by routine procedures such as extraction or distillation.

The following examples are presented to illustrate the invention.

EXAMPLES

Example 1

Preparation of 3-Thiomethylbutyraldehyde

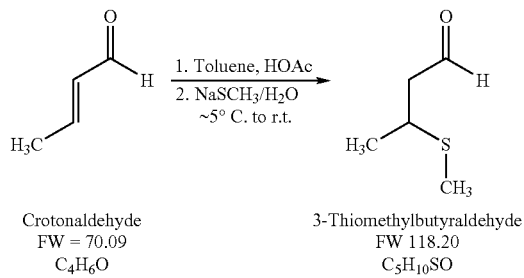

Crotonaldehyde
FW = 70.09
C₄H₆O

3-Thiomethylbutyraldehyde
FW 118.20
C₅H₁₀SO

Crotonaldehyde (21.06 grams (g), 0.30 moles), toluene (170 milliliters (mL)) and glacial acetic acid (34.4 mL, 0.60 moles (mol), 2.0 equivalents (eq)) were combined in a 500 mL three necked round bottomed flask equipped with a magnetic stir bar, thermowell with K-thermocouple, pressure equalizing addition funnel, nitrogen oil bubbler and septum. The reactor system was vented to a bleach scrubber. The clear, colorless solution was chilled in an ice bath to less than 5° C. A 15 wt % aqueous solution of sodium thiomethoxide (168.53 g of solution, 25.28 g, 0.361 mol, 1.2 eq) was added dropwise via the addition funnel during 44 minutes (min). The starting temperature was 1.4° C. The final temperature was 3.7° C. The maximum temperature realized during the addition was 4.3° C. Stirring was continued at less than 5° C. for 1 hour (h) 26 min. The ice bath was drained and the reaction mixture allowed to warm to room temperature and stirred overnight (17 h). In-process gas chromatography (GC) showed 4 area % thiomethane, 5 area % unreacted crotonaldehyde and 88 area % 3-thiomethyl butyraldehyde. Stirring was continued at room temperature for an additional 5 h 17 min. Agitation was stopped and the phases were allowed to settle. Both phases were clear and colorless. The lower aqueous phase (174.64 g, pH~6 by pHydrion paper) was removed. The upper toluene phase was washed with deionized (DI) water (30 mL) and the phases separated. The toluene phase was transferred to a 250 mL round bottom flask equipped with a magnetic stir bar and short path distillation head and receiver. The pressure was reduced to about 50 mm Hg and the heating mantle warmed to 55 to 74° C. A total of 68.20 g of distillate was removed at 25-35° C./40-60 mm Hg. GC analysis gave 98.7 area % toluene and 0.71 area % 3-thiomethyl butyraldehyde. The bottom layer (bottoms) was analyzed by GC and showed 83.3 area % toluene and 15.8 area % 3-thiomethyl butyraldehyde. The bottoms were placed in the refrigerator overnight. The bottoms were then placed under vacuum (18-20 mm Hg) and the heating mantle warmed to 50 to 60° C. It was necessary to chill the receiver with some dry ice to condense the overhead vapors. Additional volatiles were collected in the dry ice trap. The vacuum was broken when the 50 mL overhead receiver became too full. The maximum overhead temperature was 16.7° C. The contents of the receiver (33.56 g) were removed. GC analysis showed 98.1 area % toluene and 1.54 area % 3-thiomethyl butyraldehyde. The bottoms (46.13 g) were transferred to a 100 mL round bottom flask. The pressure was reduced to 18-20 mm Hg and the heating mantle warmed to 70 to 75° C. A fraction (2.54 g) boiling from 21 to 28° C. was collected. GC analysis showed 81.4 area % toluene and 17.5 area % 3-thiomethyl butyraldehyde. The 3-thiomethyl butyraldehyde was collected at 53 to 64° C./18 to 20 mm Hg and a mantle temperature of 105-118° C. A total of 26.78 g (maximum 75.4% yield) was collected. GC analysis showed 7.7 area % toluene and 89.6 area % 3-thiomethyl butyraldehyde.

Example 2

Preparation of 3-Thiomethylbutyraldehyde

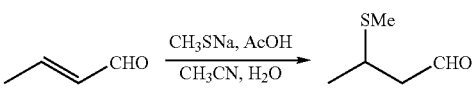

To a two-neck 25 mL round bottom flask equipped with a temperature probe, magnetic stirring, and bleach scrubber was charged in sequence 1.45 g (24.17 millimoles (mmol)) of glacial acetic acid followed by 1.44 g (20.55 mmol) of crotonaldehyde followed by 4.0 mL of acetonitrile, and the mixture was then cooled in an ice-water bath. To this mixture was continuously added (con-added) 10 g (21.40 mmol) of a 15 wt % sodium thiomethoxide in water solution over a 13 min period. The internal reaction temperature rose from 2° C. to 11° C. during the sodium thiomethoxide addition. The ice-water bath was removed and the reaction mixture was allowed to warm to ambient temperature and stirred for an additional 32 min. The reaction mixture was then heated at 50-60° C. for 3 h at which time GC analysis indicated the reaction was complete. After cooling to ambient temperature, the organic layer was separated. The aqueous layer was extracted with 2 mL of fresh acetonitrile. The combined organic layers weighed 5.55 g. GC assay of this mixture (using dipropyl phthalate as an internal standard) indicated a 3-thiomethyl butyraldehyde in-pot yield of 89%.

Example 3

Preparation of 3-Thiomethylbutyraldehyde

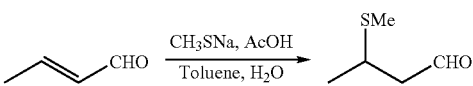

To a three-neck 100 mL round bottom flask equipped with a temperature probe, magnetic stirring, and bleach scrubber was charged in sequence 3.71 g (61.78 mmol) of glacial acetic acid followed by 3.62 g (51.65 mmol) of crotonaldehyde followed by 10 mL of toluene, and the mixture was then cooled in an ice-water bath. To this mixture was con-added 25 g (53.50 mmol) of a 15 wt % sodium thiomethoxide in water solution over a 21 min period. The internal reaction temperature rose from 2° C. to 10° C. during the sodium thiomethoxide addition. The ice-water bath was removed and the reaction mixture was allowed to warm to ambient temperature and stirred for an additional 23 min. The reaction mixture was then heated at 50-60° C. for 4.5 h at which time GC indicated the reaction was complete. After cooling to ambient temperature, the organic layer was separated. The aqueous layer was extracted with 2.5 mL of fresh toluene. The combined organic layers weighed 16.95 g. GC assay of this mixture (using dipropyl phthalate as an internal standard) indicated a 3-thiomethyl butyraldehyde in-pot yield of 92%.

Example 4

Preparation of 3-Thiomethylbutyraldehyde

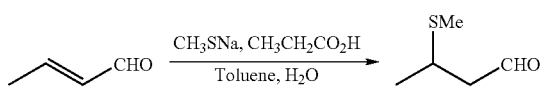

To a three-neck 100 mL round bottom flask equipped with a temperature probe, magnetic stirring, and bleach scrubber was charged in sequence 4.67 g (63.04 mmol) of propionic acid followed by 3.60 g (51.36 mmol) of crotonaldehyde followed by 10 mL of toluene, and the mixture was then cooled in an ice-water bath. To this mixture was con-added 25 g (53.50 mmol) of a 15 wt % sodium thiomethoxide in water solution over a 31 min period. The internal reaction temperature rose from 2° C. to 8° C. during the sodium thiomethoxide addition. The ice-water bath was removed and the reaction mixture was allowed to warm to ambient temperature and stirred for an additional 14 min. The reaction mixture was then heated at 50-70° C. for 4 h at which time GC indicated the reaction was complete. After cooling to ambient temperature, the organic layer was separated. The aqueous layer was extracted with 2.5 mL of fresh toluene. The combined organic layers weighed 16.68 g. GC assay of this mixture (using dipropyl phthalate as an internal standard) indicated a 3-thiomethyl butyraldehyde in-pot yield of 95%.

Example 5

Preparation of Methyl 2-phenylsulfonylethyl sulfide

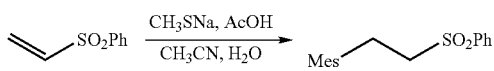

To a three-neck 50 mL round bottom flask equipped with a temperature probe, magnetic stirring, and bleach scrubber was charged in sequence 3.43 g (20.39 mmol) phenyl vinyl sulfone followed by 5 mL of acetonitrile, and the mixture was then cooled in an ice-water bath. To this mixture was then added 2.53 g (42.13 mmol) of glacial acetic acid in one portion. To this mixture was con-added 10 g (21.40 mmol) of a 15 wt % sodium thiomethoxide in water solution over a 17 min period. The internal reaction temperature rose from 14° C. to 17° C. during the sodium thiomethoxide addition. The ice-water bath was removed and the reaction mixture was heated to 50-60° C. for 3.5 h at which time liquid chromatography (LC) analysis indicated about 42% (relative area) of starting phenyl vinyl sulfone in the reaction mixture. Another 4.76 g (10.19 mmol) of a 15 wt % sodium thiomethoxide in water solution was added over a 9 min period. The reaction mixture was then stirred an additional 6.5 h at 50-60° C., and then cooled to ambient temperature and allowed to stir overnight. At this time LC analysis indicated about 7% (relative area) of starting phenyl vinyl sulfone in the reaction mixture. To the reaction mixture was added 1.37 g (23.44 mmol) of sodium chloride and the reaction phases were allowed to separate. The organic layer was concentrated on a rotary evaporator to give 3.96 g of methyl 2-phenylsulfonylethyl sulfide as a yellow oil (yield was ~90% based on theoretical yield). $^1$H NMR (300 MHz, CDCl$_3$) δ 2.1 (s, 3H), 2.78 (m, 2H), 3.35 (m 2H), 7.1 (m, 2H), 7.7 (m, 1H), 7.9 (m, 2H). $^{13}$C NMR (75.5 MHz, CDCl$_3$) δ 15.5, 26.4, 56.0, 127.9, 129.4, 134.1, 138.6.

Example 6

Preparation of 3-(Methylthio)cyclopentanone

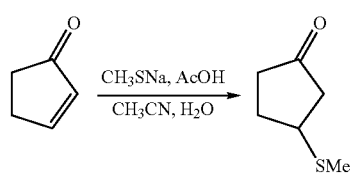

To a three-neck 50 mL round bottom flask equipped with a temperature probe, magnetic stirring, and bleach scrubber was charged in sequence 1.41 g (23.48 mmol) of glacial acetic acid followed by 1.73 g (21.07 mmol) of 2-cyclopentene-1-one followed by 4.0 mL of acetonitrile, and the mixture was then cooled in an ice-water bath. To this mixture was con-added 10 g (21.40 mmol) of a 15 wt % sodium thiomethoxide in water solution over a 9 min period. The internal reaction temperature rose from 5° C. to 8° C. during the sodium thiomethoxide addition. The ice-water bath was removed and the reaction mixture was allowed to warm to ambient temperature and stirred for an additional 1.5 h. The reaction mixture was then heated at 50-60° C. for 30 min at which time GC indicated the reaction was complete. After cooling to ambient temperature, the organic layer was separated and concentrated on a rotary evaporator to give 2.52 g of 3-(methylthio)cyclopentanone as a yellow oil (yield was ~92% based on theoretical yield). $^1$H NMR (300 MHz, CDCl$_3$) δ 2.00 (m, 1H), 2.15 (s, 3H), 2.20 (m, 2H), 2.4 (m, 2H), 2.6 (m, 1H), 3.4 (m, 1H). $^{13}$C NMR (75.5 MHz, CDCl$_3$) δ 14.4, 29.3, 37.0, 42.0, 45.2, 216.8. GC/EIMS (relative peak intensity) m/z 130 (56), 83 (37), 74 (27), 55 (100).

Example 7

Preparation of 3-Methyl-3-(methylthio)cyclopentanone

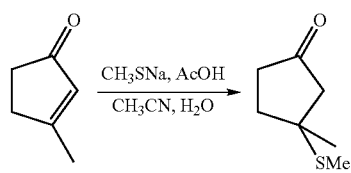

To a three-neck 50 mL round bottom flask equipped with a temperature probe, magnetic stirring, and bleach scrubber was charged in sequence 1.46 g (24.31 mmol) of glacial acetic acid followed by 1.98 g (20.59 mmol) of 3-methyl-2-cyclopentene-1-one followed by 4.0 mL of acetonitrile, and the mixture was then cooled in an ice-water bath. To this mixture was con-added 10 g (21.40 mmol) of a 15 wt % sodium thiomethoxide in water solution over a 14 min period. The internal reaction temperature rose from 3° C. to 5° C. during the sodium thiomethoxide addition. The ice-water bath was removed, and the reaction mixture was allowed to warm to ambient temperature and stirred for an additional 22 min. The reaction mixture was then heated at 50-60° C. for 15.5 h at which time GC indicated the reaction contained a 3-methyl-2-cyclopentene-1-one to 3-methyl-3-(methylthio)cyclopentanone peak ratio of 3.7 to 1. To this mixture at 50° C. was con-added another 1.28 g (21.32 mmol) of glacial acetic acid followed by 10 g (21.40 mmol) of a 15 wt % sodium thiomethoxide in water solution over a 30 min period. The reaction mixture was stirred another 6.5 h at which time GC indicated the reaction contained a 3-methyl-2-cyclopentene-1-one to 3-methyl-3-(methylthio)cyclopentanone peak ratio of 1.2 to 1. To this mixture at 50° C. was con-added another 2.79 g (46.46 mmol) of glacial acetic acid followed by 10 g (21.40 mmol) of a 15 wt % sodium thiomethoxide in water solution over a 26 min period. The reaction mixture was stirred another 15 h at which time GC indicated the reaction contained a 3-methyl-2-cyclopentene-1-one to 3-methyl-3-(methylthio)cyclopentanone peak ratio of 1.1 to 1. After cooling to ambient temperature, the organic layer was separated and concentrated on a rotary evaporator to give 1.0 g of 3-methyl-3-(methylthio)cyclopentanone plus starting material as a yellow oil. GC/EIMS (relative peak intensity) for 3-methyl-3-(methylthio)-cyclopentanone m/z 144 (53), 97 (65), 69 (100), 55 (55).

Example 8

Preparation of 4-(Methylthio)pentan-2-one

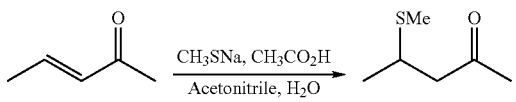

To a three-neck 50 mL round bottom flask equipped with a temperature probe, magnetic stirring, and bleach scrubber was charged in sequence 1.46 g (24.31 mmol) of glacial acetic acid followed by 1.73 g (21.57 mmol) of 65% 3-penten-2-one (contains ~30% mesityl oxide), followed by 4.0 mL of acetonitrile, and the mixture was then cooled in an ice-water bath. To this mixture was con-added 10 g (21.40 mmol) of a 15 wt % sodium thiomethoxide in water solution over a 23 min period. The internal reaction temperature rose from 2° C. to 4° C. during the sodium thiomethoxide addition. The ice-water bath was removed, and the reaction mixture was allowed to warm to ambient temperature and stirred for an additional 1 h. The reaction mixture was then heated at 50-60° C. for 30 min at which time GC peak area indicated a 3-pentene-2-one: mesityl oxide:4-(methylthio)pentan-2-one ratio of 4:16:80. After cooling to ambient temperature, the organic layer was separated and concentrated on a rotary evaporator to give 2.10 g of 4-(methylthio)pentan-2-one as a yellow oil (yield was ~77% based on theoretical yield). $^1$H NMR (300 MHz, CDCl$_3$) δ 1.3 (d, J=7 Hz, 3H), 2.1 (s, 3H), 2.2 (s, 3H), 2.6 (dd, J=17, 8 Hz, 1H), 2.8 (dd, J=17, 8 Hz, 1H), 3.2 (m, 1H). $^{13}$C NMR (75.5 MHz, CDCl$_3$) δ 13.4, 20.9, 30.5, 36.2, 50.4, 206.7. GC/EIMS (relative peak intensity) m/z. 132 (100), 89 (93), 75 (99).

Example 9

Preparation of Ethyl 3-(methylthio)-3-phenylpropanoate

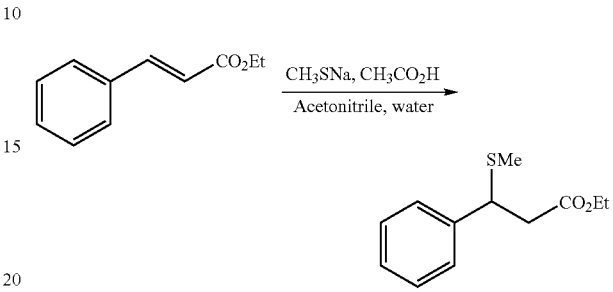

To a three-neck 100 mL round bottom flask equipped with a temperature probe, magnetic stirring, and bleach scrubber was charged in sequence 3.46 g (57.62 mmol) of glacial acetic acid followed by 467 milligrams (mg) (2.65 mmol) of ethyl cinnamate, followed by 20 mL of acetonitrile. To this ambient temperature mixture was con-added 20 g (42.80 mmol) of a 15 wt % sodium thiomethoxide in water solution over a 24 min period. The internal reaction temperature rose from 18° C. to 22° C. during the sodium thiomethoxide addition. The reaction mixture was then heated to 50-60° C. for 22 h at which time GC peak area indicated a ethyl cinnamate to ethyl 3-(methylthio)-3-phenylpropanoate of 1.3:1. After cooling to ambient temperature, the organic layer was separated and concentrated on a rotary evaporator to give 870 mg of mixture containing predominantly ethyl 3-(methylthio)-3-phenylpropanoate as a wet yellow oil. (Purity was ~42% based on GC relative area). GC/EIMS (relative peak intensity) m/z. 224 (6) 176 (47) 151 (58) 91 (100) 77 (37).

Example 10

Preparation of 3-(Methylthio)cyclohexanone

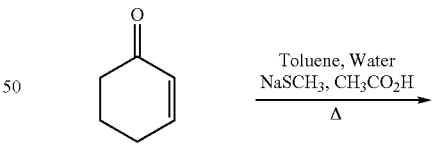

Cyclohex-2-enone
Chemical Formula: C$_6$H$_8$O
Molecular Weight: 96.13

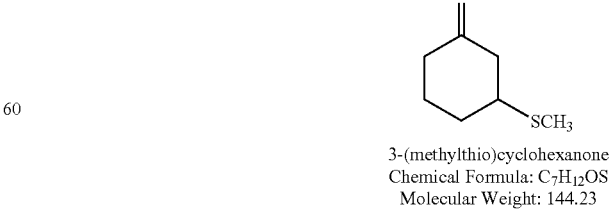

3-(methylthio)cyclohexanone
Chemical Formula: C$_7$H$_{12}$OS
Molecular Weight: 144.23

Cyclohex-2-enone (3.80 g, 95% Aldrich, 39.5 mmol uncorrected), toluene (15.31 g, HPLC grade) and glacial acetic acid (2.85 g, 47.4 mmoles, 1.20 eq, 99.7+% Aldrich) were combined in a 50 mL 3-necked round bottom flask equipped with a magnetic stirrer, reflux condenser with nitrogen oil bubbler vented to a bleach scrubber, thermometer with Therm-o-watch controller and septum. To the stirred solution was added 15 wt % sodium thiomethoxide (19.4 g of solution, 2.91 g, 41.5 mmol, 1.05 eq of $NaSCH_3$) in portions via syringe during 19 min. The reaction temperature increased from 28.0° C. to 36.4° C. during the addition. The two-phase mixture was stirred at ambient temperature overnight. The reaction mixture was heated to about 50° C. and stirred for 7.5 h. The mixture was then allowed to cool to room temperature with stirring overnight. The phases were allowed to settle for 30 min. The lower aqueous phase was removed. The upper organic phase was washed with water (2×10 mL), dried through a cone of anhydrous magnesium sulfate and concentrated on the rotary evaporator (29 in. Hg vacuum/48° C.) to afford 4.91 g of 3-(methylthio)cyclohexanone as a clear pale yellow oil. Area % conversion by GC 95%. Raw area % 91.1%. Mass recovery 86%.

Example 11

Preparation of 3-Methyl-3-(methylthio)cyclohexanone

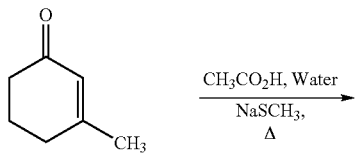

3-Methylcyclohex-2-enone
Chemical Formula: $C_7H_{10}O$
Molecular Weight: 110.15

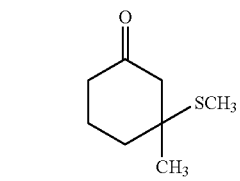

3-Methyl-3-(methylthio)cyclohexanone
Chemical Formula: $C_8H_{14}OS$
Molecular Weight: 158.26

3-Methylcyclohex-2-enone (1.23 g, 11.2 mmol) and glacial acetic acid (9.48 g, 158 mmol) were combined in a 25 mL three necked round bottom flask equipped with a reflux condenser with nitrogen oil bubbler vented to a bleach scrubber, magnetic stirrer, thermowell with K-thermocouple, septum and heating mantle. To the stirred solution was added 15 wt % sodium thiomethoxide (7.87 g of solution, 1.18 g, 16.8 mmol, 1.50 eq of $NaSCH_3$) in portions via syringe during 8 min while maintaining the temperature between 16 and 18° C. The resulting reaction mixture was stirred at room temperature overnight. The reaction mixture was heated to about 50° C. and stirred for 5 h. Additional 15 wt % sodium thiomethoxide (5.25 g of solution, 0.79 g, 11.3 mmol of $NaSCH_3$) was added in portions via syringe during 12 min. Stirring continued at about 50° C. overnight. Analysis by GC indicated an area % conversion to 3-methyl-3-(methylthio)cyclohexanone of 27 area %. Raw area % by GC was 20.4%.

Example 12

Preparation of 2-Methyl-3-(methylthiomethyl)butanal

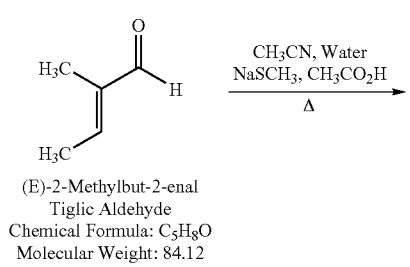

(E)-2-Methylbut-2-enal
Tiglic Aldehyde
Chemical Formula: $C_5H_8O$
Molecular Weight: 84.12

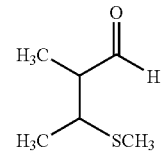

2-Methyl-3-(methylthio)butanal
Chemical Formula: $C_6H_{12}OS$
Molecular Weight: 132.22

Tiglic aldehyde (2.44 g, 29.0 mmol), glacial acetic acid (3.48 g, 58.0 mmol) and acetonitrile (9.76 g) were combined in 50 mL 3-necked round bottom flask equipped with a magnetic stirrer, reflux condenser with nitrogen oil bubbler vented to a bleach scrubber, thermometer with Therm-o-watch controller and septum. To the stirred solution was added 15 wt % sodium thiomethoxide (20.3 g of solution, 3.05 g, 43.5 mmol, 1.5 eq of $NaSCH_3$) in portions via syringe during 20 min. The reaction temperature increased from 21.0° C. to 26.8° C. during the addition. The reaction mixture was heated to about 50° C. and stirred an additional 18 h. The reaction mixture was cooled to room temperature. Additional glacial acetic acid (1.74 g, 29.0 mmol, 1.0 eq) was added. To the stirred mixture was added additional 15 wt % sodium thiomethoxide (10.2 g of solution, 1.53 g, 21.8 mmol, 0.75 eq of $NaSCH_3$) in portions via syringe during 10 min. The internal temperature increased from 23.1° C. to 28.0° C. The reaction mixture was heated to about 50° C., stirred for 5.75 h, cooled to room temperature and the phases allowed to separate overnight. The lower aqueous phase was transferred to a separatory funnel and extracted with methylene chloride (4×15 mL). The upper organic phase from the reactor was combined with the methylene chloride extracts and washed with saturated aqueous sodium bicarbonate (25 mL), water (25 mL), dried through a cone of anhydrous magnesium sulfate and concentrated on the rotary evaporator to afford 3.56 g (93%) of crude 2-methyl-3-(thiomethyl)butanal as a pale yellow oil. Crude area % by GC was 95%.

Example 13

Preparation of 2-Ethyl-3-thiomethylpropanal

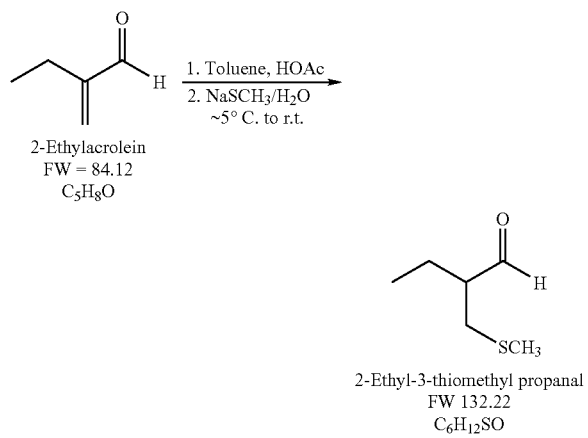

2-Ethylacrolein
FW = 84.12
$C_5H_8O$

1. Toluene, HOAc
2. NaSCH₃/H₂O
~5° C. to r.t.

2-Ethyl-3-thiomethyl propanal
FW 132.22
$C_6H_{12}SO$

2-Ethyl acrolein (2.38 g, 90% tech. grade, Alfa Aesar, 2.14 g, 25.4 mmol), toluene (10 mL) and glacial acetic acid (3.05 g, 2.91 mL, 50.8 mmol, 2.0 eq) were combined in a 25-mL three necked round bottomed flask equipped with a magnetic stir bar, thermowell with K-thermocouple, reflux condenser with nitrogen oil bubbler and septum. The reactor system was vented to a bleach scrubber. The clear, colorless solution was chilled in an ice bath with stirring. To the well stirred, chilled solution was added 15 wt % aqueous sodium thiomethoxide (17.8 g of solution, 2.67 g, 38.1 mmol, 1.5 eq) in portions via syringe during 15 min. The starting temperature was 3.7° C. The final temperature was 4.4° C. The maximum temperature realized during the addition of 5.9° C. Stirring was continued and the reaction mixture was allowed to slowly warm to room temperature. Stirring was continued at room temperature over the weekend. The lower aqueous phase was removed. The toluene phase was washed with saturated aqueous sodium bicarbonate solution (3 mL) and dried through a cone of anhydrous magnesium sulfate. The reactor was rinsed with toluene (2×3 mL) and each rinse filtered through the cone of magnesium sulfate. The combined filtrate mass was 12.84 g. GC analysis indicated the consumption of the 2-ethyl acrolein and the formation of a new compound which was confirmed by GC-MS as the desired 2-ethyl-3-thiomethylpropanal. The filtrate was transferred to a 25-mL round bottom flask equipped with a magnetic stir bar and fitted with a short path distillation head and receiver. The heating mantle was warmed to about 42° C. and the pressure slowly reduced to about 50 mm Hg. The toluene was removed at an overhead temperature of 26 to 30° C. and a maximum mantle temperature of 60° C. The system was allowed to cool and the receiver was replaced. The pressure was reduced to about 22 mm Hg. The 2-ethyl-3-thio-methylpropanal was collected at 77 to 83° C./22 mm Hg at a mantle temperature of 99 to 132° C. A total of 2.41 g (72%) of 2-ethyl-3-thiomethylpropanal was isolated as a clear, colorless liquid. GC analysis gave 86 area % purity.

What is claimed is:

1. A process for the preparation of alkylthio substituted aldehydes, ketones, and esters of formula I

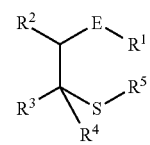

wherein

E represents CO;

$R^1$ represents H, $C_1$-$C_8$ alkyl, $C_1$-$C_8$ alkoxy or aryl; and $R^2$, $R^3$, $R^4$ and $R^5$ independently represent H, $C_1$-$C_8$ alkyl or aryl which consists essentially of reacting an α,β-unsaturated carbonyl compound of the formula II

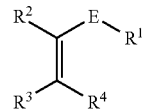

wherein

E, $R^1$, $R^2$, $R^3$ and $R^4$ are as previously defined with a sodium or potassium thiolate of formula III

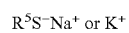

$R^5S^-Na^+$ or $K^+$ (III)

wherein $R^5$ is as previously defined in the presence of a $C_1$-$C_4$ alkane carboxylic acid and water.

2. A process according to claim 1 wherein $R^1$ represents H.

3. A process according to claim 1 wherein $R^2$ represents H, $CH_3$, or $CH_2CH_3$.

4. A process according to claim 1 wherein $R^3$ is $CH_3$ or $CH_2CH_3$.

5. A process according to claim 1 wherein $R^4$ is H.

6. A process according to claim 1 wherein $R^5$ is $CH_3$.

7. A process according to claim 1 wherein said process is conducted with an organic co-solvent.

8. A process according to claim 1 wherein approximately equimolar quantities of α,β-unsaturated carbonyl and sodium or potassium thiolate are employed in said process.

9. A process according to claim 8 wherein a 1-50 percent stoichiometric excess of sodium or potassium thiolate is employed in said process.

10. A process according to claim 8 wherein a 2-30 percent stoichiometric excess of sodium or potassium thiolate is employed in said process.

11. A process according to claim 8 wherein a 3-20 percent stoichiometric excess of sodium or potassium thiolate is employed in said process.

12. A process according to claim 1 wherein said alkane carboxylic acid is present in an amount equal to about 1 to 10 equivalents with respect to the α,β-unsaturated carbonyl or the sodium or potassium thiolate.

13. A process according to claim 1 wherein said alkane carboxylic acid is present in an amount equal to about 1.0 to 1.7 equivalents with respect to the α,β-unsaturated carbonyl or the sodium or potassium thiolate.

14. A process according to claim 1 wherein said alkane carboxylic acid is present in an amount equal to about 1.1 to 1.6 equivalents with respect to the α,β-unsaturated carbonyl or the sodium or potassium thiolate.

15. A process according to claim 1 wherein said process is conducted at a temperature from about 0° C. to about 70° C.

16. A process according to claim 1 wherein said process is conducted at a temperature from about 5° C. to about 60° C.

17. A process according to claim 1 wherein said process is conducted under a substantially oxygen-free atmosphere.

18. A process according to claim 17 wherein said process is conducted under nitrogen.

19. A process according to claim 1 wherein said α,β-unsaturated carbonyl and the alkane carboxylic acid are mixed together and chilled to about 0 to about 5° C. then an aqueous solution of sodium or potassium thiolate is added.

20. A process according to claim 1 wherein:
$R^1$ is H;
$R^2$ is H, $CH_3$, or $CH_2CH_3$;
$R^3$ is $CH_3$ or $CH_2CH_3$;
$R^4$ is H;
$R^5$ is $CH_3$;
a 3-20 percent stoichiometric excess of sodium or potassium thiolate is employed in said process;
said alkane carboxylic acid is present in an amount equal to about 1.1 to 1.6 equivalents with respect to the α,β-unsaturated carbonyl or the sodium or potassium thiolate; and
said process is conducted at a temperature from about 5° C. to about 60° C.

* * * * *